United States Patent [19]

Marquardt

[11] Patent Number: 5,381,789
[45] Date of Patent: Jan. 17, 1995

[54] IONIZER FOR THE IONIZATION OF OXYGEN IN OXYGEN THERAPY

[76] Inventor: Klaus Marquardt, 7522 Philippsburg 2, Am Sandrain 10, Germany

[21] Appl. No.: 728,191

[22] Filed: Jul. 10, 1991

[30] Foreign Application Priority Data

Jul. 13, 1990 [DE] Germany ............... 4022393

[51] Int. Cl.⁶ .............................................. A61M 15/02
[52] U.S. Cl. ...................................... 128/202.25; 128/908
[58] Field of Search .................... 128/202.25, 908; 422/186.07

[56] References Cited

U.S. PATENT DOCUMENTS

| | | | |
|---|---|---|---|
| 430,387 | 6/1890 | Kennedy | 128/202.25 |
| 2,415,659 | 2/1947 | Steel | 128/202.25 |
| 2,920,622 | 1/1960 | Steel | 128/202.25 |
| 3,096,762 | 9/1963 | Winchell | 128/202.25 |
| 3,232,292 | 2/1966 | Schaefer | 128/202.25 |
| 3,717,148 | 2/1973 | Svab | 128/202.25 |

FOREIGN PATENT DOCUMENTS

| | | | |
|---|---|---|---|
| 1019424 | 1/1953 | France | 128/202.25 |
| 1073107 | 9/1954 | France | 128/202.25 |
| 634919 | 9/1936 | Germany | 128/202.25 |
| 30965 | 9/1933 | Netherlands | 128/202.25 |
| 1045883 | 10/1966 | United Kingdom . | |

Primary Examiner—Edgar S. Burr
Assistant Examiner—Aaron J. Lewis
Attorney, Agent, or Firm—Staas & Halsey

[57] ABSTRACT

An ionizer for the ionization of oxygen during any type of oxygen therapy. The ionizer contains an ionizing unit inside a housing. The housing has a grounded contact safety screen mounted thereon by means of a conducting metal ring and a high-ohmic resistor. A glass flask is mounted or screwed onto the housing to serve as a connection between the face mask and the ionizer. The housing has a projecting socket enclosed in a conducting metal cylinder connected to the high-ohmic resistor. The ionizing unit includes ionizing needles located directly adjacent the contact safety screen. Sufficient ionization of oxygen occurs without the production of ozone.

25 Claims, 1 Drawing Sheet

IONIZER FOR THE IONIZATION OF OXYGEN IN OXYGEN THERAPY

BACKGROUND OF THE INVENTION

This invention is directed to an ionizer for ionizing oxygen used in all types of oxygen therapy.

Ionized oxygen inhalation therapy ($IO_2IT$) consists of a brief inhalation with a defined mixture of medical oxygen and selectively negative or positive oxygen ions for therapeutic or preventive purposes. $IO_2IT$ refers to partial and polar ionization of medical oxygen with a suitable oxygen ionization device for inhalation therapies.

Almost without exception, oxygen ionizers available on the market produce many millions of ions per $cm^3$/sec. An insufficient amount of these ions reaches an inhalation mask, however, because over 90% of the ions are discharged in an inlet tube between the ionizer and a face mask. A higher compressive stress feed can be used to release more ions; ozone, however, which is classified as a respiratory poison, is produced as a by-product.

Ionizers which attempt to solve this problem, ionize directly in front of the inhalation mask and use plastic as a contact safety device. Plastic, regardless of the type, destroys ionization. Therefore, such solutions must be deemed unsatisfactory.

SUMMARY OF THE INVENTION

An object of the present invention is to provide an ionizer where ionization takes place directly in front of a face mask.

It is another object of the present invention to provide an ionizer in which plastic is not used in an ionization field extending to the face mask, so that sufficient ions which are ozone free are available in front of the face mask.

The above-mentioned objects of the present invention are obtained by providing an ionizer for the ionization of oxygen in oxygen therapies comprising an ionization unit contained in a housing having a grounded contact safety screen mounted thereon by means of a conducting metal ring and a high ohmic resistor. A glass flask is mounted thereto and acts as a connection between the face mask and the ionizer. The face mask is attached directly to the end of the ionizer. Glass is the material used for the mask mounting. A contact safety device is provided and is made of high-grade steel. The contact safety device is grounded by a high-ohmic resistor of approximately 20.000 Mega-Ohm ohms or more. A high voltage, approximately 5 500 Volt volts applied to the device by way of a high voltage cable is below the ozone-creating level which is 6 700 Volt.

The ionization unit is designed to be contained in the ionizer housing. The grounded contact safety screen is fastened to the ionizer housing by means of the conducting metal ring and the high-ohmic resistor. The glass flask is mounted or screwed into the ionizer housing to connect the face mask and the ionizer.

The housing features a socket on one end. The socket is enclosed in a conducting metal cylinder. A hollow chamber, in which the ionization unit is arranged, is provided inside the housing.

Ionization needles are arranged directly adjacent the contact safety screen. The ionization needles are formed on or placed in a socket mounting in the hollow chamber. The socket mounting is connected to a mounting bushing for attaching the high-voltage cable.

Oxygen entry bores are located in the housing floor. The mounting bushing for the high-voltage cable is inserted into the entry bores and is mounted in or on the housing floor. Between the metal ring and the contact safety screen is a fixed connection which is preferably made by a soldering point.

VA2 steel (a high grade steel) is the preferred material for the ionizing needles and for the mounting bushing. The contact safety screen is also made of a high-grade steel.

These objects, together with other objects and advantages which will be subsequently apparent, reside in the details of construction and operation as more fully hereinafter described and claimed, reference being had to the accompanying drawings forming a part hereof, wherein like reference numerals refer to like parts throughout.

DESCRIPTION OF THE PREFERRED EMBODIMENT

Figure 1:
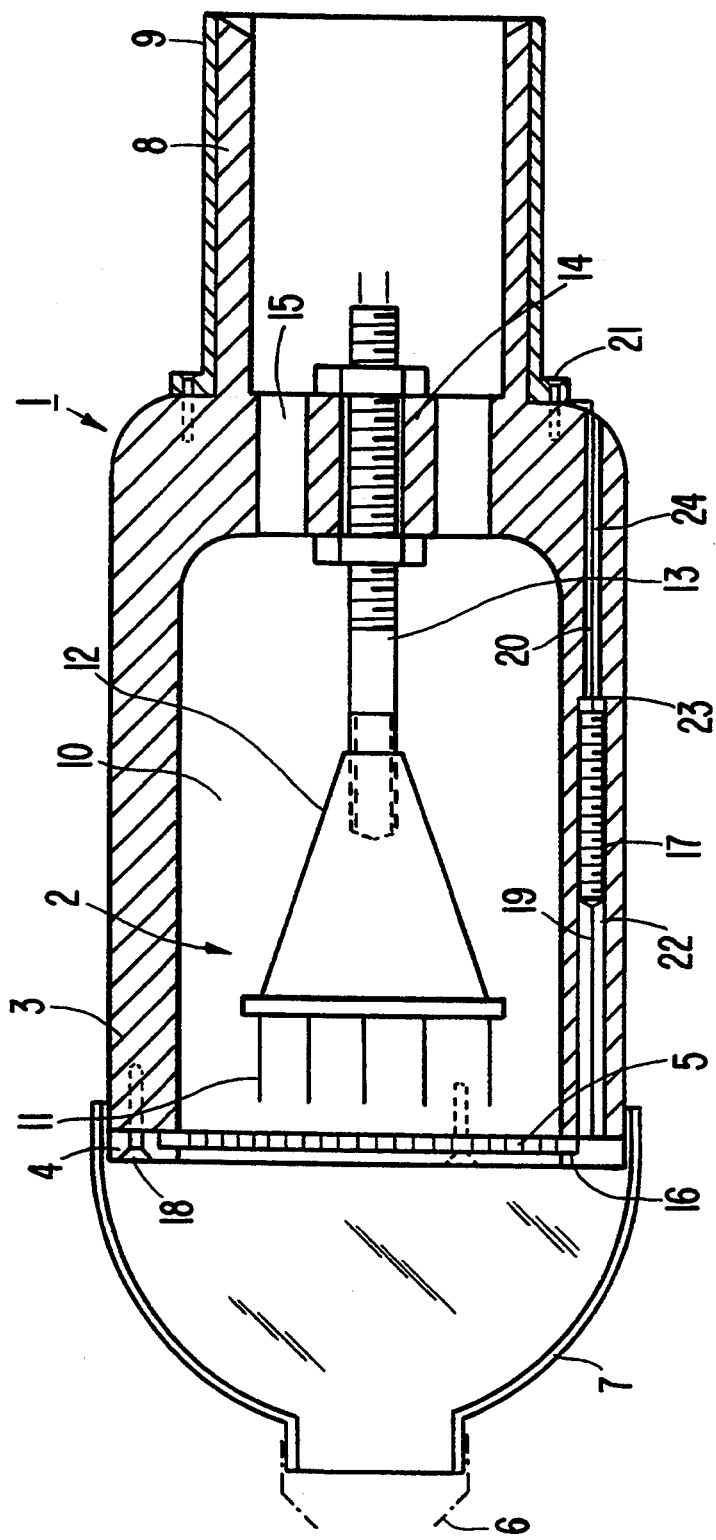
FIG. 1 is an ionizer for the ionization of oxygen during oxygen therapy according to the present invention.

FIG. 1 is a diagram of an ionizer 1 according to the present invention. The ionizer 1 includes a housing having a hollow chamber 10. The housing 3 is tapered on one end. The tapered end features a projecting socket 8 which is enclosed in a conducting metal cylinder 9. A housing floor 14 located at the taper of the housing contains entry bores 15 for the flow of oxygen. A mounting bushing 13 extends through the housing floor 14 for inserting a high voltage cable which connects to a socket mounting 12 having ionization needles 11 extending therefrom. The ionization needles 11 are arranged directly adjacent to a contact safety screen 5. The contact safety screen 5 is mounted on the housing 3 by a conducting metal ring 4 held in place with screws 18. The conducting metal ring 4 and contact safety screen 5 are connected together by, for example, a soldering point 16.

A cable 19 is connected to the soldering point 16 and to a first end of a high-ohmic resistor 17. A second end of the resistor 17 has a cable splice 20 connected thereto. The cable splice 20 is connected to screw means 21 which mounts the conducting metal cylinder 9 on the housing 3. The cable 19, resistor 17 and cable splice 20 form a contact safety device which prevents unwanted shocks.

In the embodiment of the present invention shown in FIG. 1, the high-ohmic resistor 17 is set in a sleeve 22 in the housing 23. An entry bore 24 connects with the sleeve 22 to conduct the cable splice 20 therethrough to connect the metal cylinder 9.

The face mask 6, indicated by the broken line, is inserted into the glass flask 7. The glass flask 7 is connected to the housing 3 by means of a screw coupling or similar connection, wherein any suitable sealing material can be used.

In the present invention, an ionizer is created which, by the application of the individual components and their arrangement according to the invention, provides an efficient yield of ionized oxygen for inhalation at the face mask. This is because plastic, which destroys ionization, is not used as a contact safety device; rather, a metal grounded contact safety device is provided. This prevents ozone formation and provides the face mask with a sufficient amount of ions.

The foregoing is considered as illustrative only of the principles of the present invention. Since numerous modifications and changes will readily occur to those skilled in the art, it is not desired to limit the invention to the exact construction and application shown and described. Accordingly, all suitable modifications and equivalents may be resorted to, falling within the scope of the invention and the appended claims and their equivalents.

What is claimed:

1. An ionizer, including a face mask, for the ionization of oxygen during any type of oxygen therapy, comprising:
   a housing;
   a conducting metal ring attached to said housing;
   an ionization unit contained in said housing;
   a grounded contact safety screen mounted to said housing by means of said conducting metal ring;
   a high-ohmic resistor operatively connected to said conducting metal ring; and
   a glass flask mounted on said housing for connecting the face mask to the ionizer.

2. An ionizer according to claim 1, wherein said housing comprises:
   a tapered end including a projecting socket; and
   a conducting metal cylinder enclosing said projecting socket.

3. An ionizer according to claim 2, wherein said housing further comprises a hollow chamber in which said ionization unit is located.

4. An ionizer according to claim 3, wherein said ionization unit comprises a socket mounting.

5. An ionizer according to claim 4, further comprises ionization needles inserted into said socket mounting directly adjacent said contact safety screen.

6. An ionizer according to claim 5, further comprising:
   a mounting bushing connected to said socket mounting; and
   a high voltage cable connected to said socket mounting by said mounting bushing.

7. An ionizer according to claim 6, further comprising:
   a housing floor; and
   oxygen entry bores located in said housing floor.

8. An ionizer according to claim 7, wherein said mounting bushing extends through said housing floor and is secured in said housing floor.

9. An ionizer according to claim 8, wherein said metal ring and said contact safety screen are fixedly connected together.

10. An ionizer according to claim 9, wherein the fixed connection come, rises a soldering point.

11. An ionizer according to claim 10, wherein said ionization needles comprise high grade steel.

12. An ionizer according to claim 11, wherein said mounting bushing comprises high grade steel.

13. An ionizer according to claim 12, wherein said contact safety screen comprises high-grade steel.

14. An ionizer according to claim 1, wherein said housing further comprises a hollow chamber in which said ionization unit is located.

15. An ionizer according to claim 14, wherein said ionization unit comprises a socket mounting.

16. An ionizer according to claim 15, further comprising ionization needles inserted into said socket mounting directly adjacent said contact safety screen.

17. An ionizer according to claim 16, further comprising:
   a mounting bushing connected to said socket mounting; and
   a high voltage cable connected to said socket mounting by said mounting bushing.

18. An ionizer according to claim 17, further comprising:
   a housing floor; and
   oxygen entry bores located in said housing floor.

19. An ionizer according to claim 18, wherein said mounting bushing extends through said housing floor and is secured in said housing floor.

20. An ionizer according to claim 19, wherein said metal ring and said contact safety screen are fixedly connected together.

21. An ionizer according to claim 20, wherein the fixed connection comprises a soldering point.

22. An ionizer according to claim 21, wherein said ionization needles comprise high grade steel.

23. An ionizer according to claim 22, wherein said contact safety screen comprises high-grade steel.

24. An ionizer for the ionization of oxygen during oxygen therapies, comprising:
   a face mask;
   a glass flask coupled to said face mask;
   a housing, coupled to said glass flask, having first and second ends a hollow interior, and a floor having a bore hole therein;
   a conducting metal ring coupled to the first end of said housing;
   a contact safety screen located over the first end of said housing and held in place by said conducting metal ring;
   an ionization unit inside said housing, comprising:
      a socket mounting having first and second ends;
      ionization needles connected to the first end of said socket mounting and adjacent said contact safety screen;
      a mounting bushing having a first end mounting the second end of said socket mounting and having a second end connected to said housing floor; and
      a screw inserted into said mounting bushing;
   a projecting socket coupled to the second end of said housing and having said screw extending therethrough; and
   a conducting metal cylinder enclosing said projecting socket.

25. An ionizer according to claim 24, wherein said housing includes a sleeve having:
   a cable inserted therein having a first end connected to said safety screen and having a second end;
   a resistor having a first end connected to the second end of said cable and having a second end; and
   a cable splice connected to the second end of said resistor.

* * * * *